(12) United States Patent
Liu

(10) Patent No.: US 10,399,120 B2
(45) Date of Patent: Sep. 3, 2019

(54) ULTRASOUND PROBE

(71) Applicant: Qisda Corporation, Taoyuan (TW)

(72) Inventor: Jian-Hung Liu, New Taipei (TW)

(73) Assignee: Qisda Corporation, Taoyuan (TW)

( * ) Notice: Subject to any disclaimer, the term of this patent is extended or adjusted under 35 U.S.C. 154(b) by 314 days.

(21) Appl. No.: 15/211,019

(22) Filed: Jul. 15, 2016

(65) Prior Publication Data

US 2017/0014866 A1  Jan. 19, 2017

(30) Foreign Application Priority Data

Jul. 16, 2015  (TW) .............................. 104123046 A

(51) Int. Cl.
| | | |
|---|---|---|
| *B06B 1/02* | (2006.01) | |
| *A61B 8/00* | (2006.01) | |
| *G01N 29/24* | (2006.01) | |
| *G01N 29/34* | (2006.01) | |

(52) U.S. Cl.
CPC .......... *B06B 1/0215* (2013.01); *A61B 8/4461* (2013.01); *G01N 29/2437* (2013.01); *G01N 29/2456* (2013.01); *G01N 29/348* (2013.01); *B06B 2201/55* (2013.01); *B06B 2201/76* (2013.01); *G01N 2291/02475* (2013.01)

(58) Field of Classification Search
CPC ................ B06B 1/0215; A61B 8/4461; G01N 29/2437; G01N 29/2456
See application file for complete search history.

(56) References Cited

U.S. PATENT DOCUMENTS

| | | | |
|---|---|---|---|
| 5,738,098 A | 4/1998 | Brock-Fisher et al. | |
| 5,834,687 A | 11/1998 | Talbot et al. | |
| 6,182,341 B1 | 2/2001 | Talbot et al. | |
| 6,540,677 B1 | 4/2003 | Angelsen et al. | |
| 8,382,689 B2 | 2/2013 | Sliwa et al. | |
| 2006/0142659 A1* | 6/2006 | Okazaki ................ | B06B 1/0622 |
| | | | 600/459 |
| 2007/0016064 A1* | 1/2007 | Yamashita ............... | A61B 8/14 |
| | | | 600/459 |
| 2008/0303381 A1* | 12/2008 | Yuuya ...................... | C08K 3/22 |
| | | | 310/327 |
| 2012/0271172 A1* | 10/2012 | Komuro ................... | A61B 8/06 |
| | | | 600/441 |
| 2014/0031693 A1* | 1/2014 | Solek ................... | A61B 8/4494 |
| | | | 600/447 |
| 2014/0096610 A1* | 4/2014 | Ha ......................... | G10K 11/00 |
| | | | 73/632 |
| 2014/0276079 A1* | 9/2014 | Yamagata ............... | A61B 8/12 |
| | | | 600/459 |

FOREIGN PATENT DOCUMENTS

CN        101422376 A      5/2009

OTHER PUBLICATIONS

Office action of counter part application by Taiwan Patent Office dated Jun. 5, 2016.

* cited by examiner

*Primary Examiner* — Bryan P Gordon

(57) ABSTRACT

An ultrasound probe including a matching element, a backing layer, a piezoelectric element and a driver is provided. The piezoelectric element is disposed between the matching element and the backing layer. The driver generates a coding wave inputted to the piezoelectric element, such that the piezoelectric element outputs a focusing sonic wave field along a short axis.

8 Claims, 3 Drawing Sheets

ULTRASOUND PROBE

This application claims the benefit of Taiwan application Serial No. 104123046, filed Jul. 16, 2015, the subject matter of which is incorporated herein by reference.

BACKGROUND OF THE INVENTION

Field of the Invention

The invention relates in general to an ultrasound probe, and more particularly to an ultrasound probe capable of generating a focusing sonic wave field.

Description of the Related Art

Normally, the ultrasound probe uses an acoustic lens to complete the focusing in a short axis to detect the tissue of an analyte. The acoustic lens is normally formed of a room temperature vulcanized silicone rubber (RTV). Since materials of the same kind are subject to high attenuation, it has become a prominent task for the industries to provide a new method for focusing in a short axis.

SUMMARY OF THE INVENTION

The invention is directed to an ultrasound probe enabling the piezoelectric element to receive a coding wave to output a focusing sonic wave field along a short axis.

According to one embodiment of the present invention, an ultrasound probe is provided. The ultrasound probe includes a matching element, a backing layer, a piezoelectric element and a driver. The piezoelectric element is disposed between the matching element and the backing layer. The driver generates a coding wave inputted to the piezoelectric element, such that the piezoelectric element outputs a focusing sonic wave field along a short axis.

According to another embodiment of the present invention, an ultrasound probe is provided. The ultrasound probe includes a matching element, a backing layer, a piezoelectric element and a driver. The piezoelectric element is disposed between the matching element and the backing layer and has a variable thickness along a short axis. The driver generates an adjustable coding wave inputted to the piezoelectric element, such that the piezoelectric element outputs a focusing sonic wave field correspondingly modulated according to the adjustment of the coding wave and the thickness of the piezoelectric element.

According to an alternate embodiment of the present invention, an ultrasound probe is provided. The ultrasound probe includes a matching element, a backing layer, a piezoelectric element and a driver. The piezoelectric element is disposed between the matching element and the backing layer. The matching element does not have any acoustic lenses disposed thereon, and the driver generates a wave signal inputted to the piezoelectric element, such that the piezoelectric element outputs a focusing sonic wave field along a short axis.

The above and other aspects of the invention will become better understood with regard to the following detailed description of the preferred but non-limiting embodiment (s). The following description is made with reference to the accompanying drawings.

DETAILED DESCRIPTION OF THE INVENTION

Figure 1:
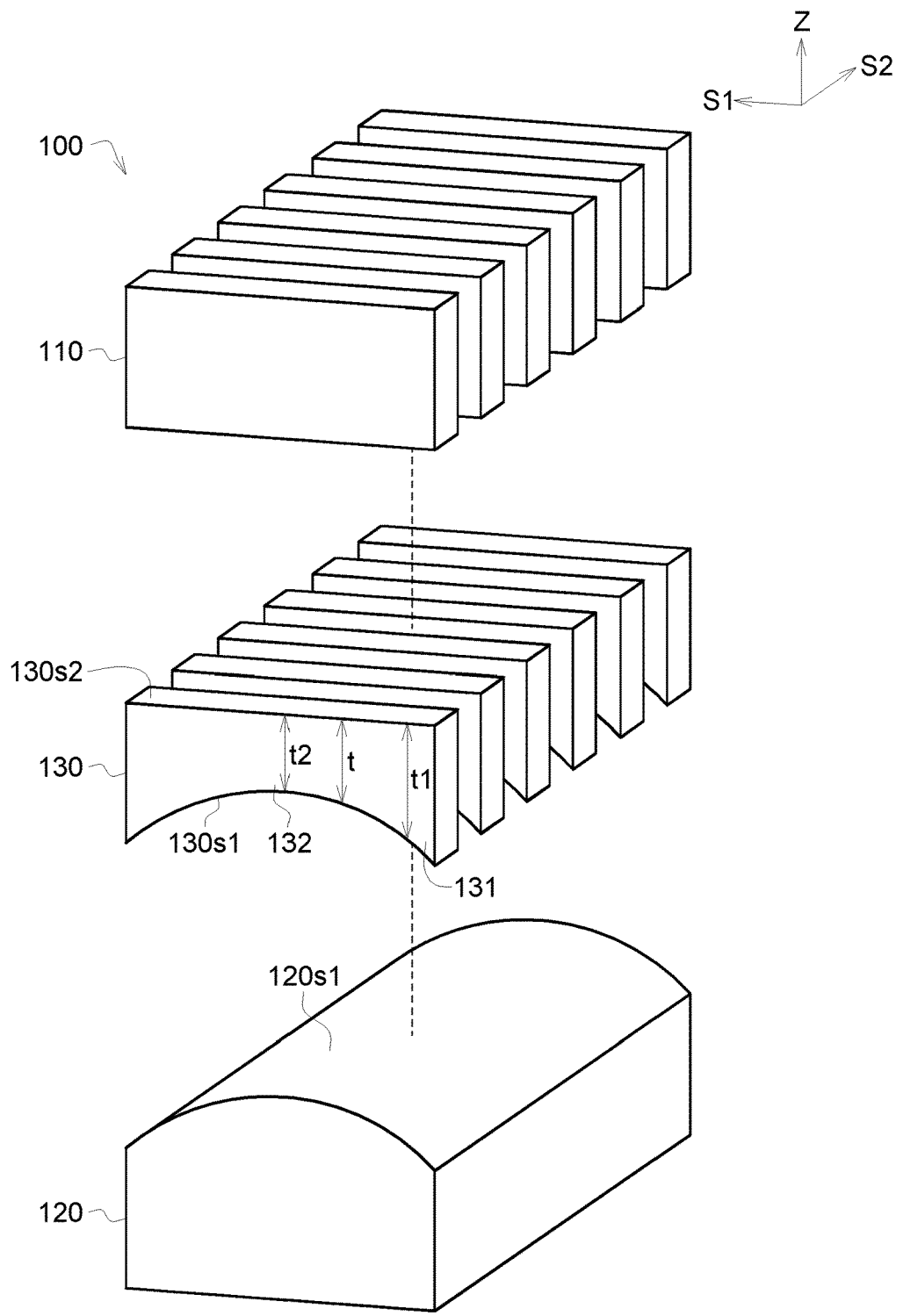
FIG. 1 is a decomposition diagram of an ultrasound probe according to an embodiment of the invention.
Figure 2:
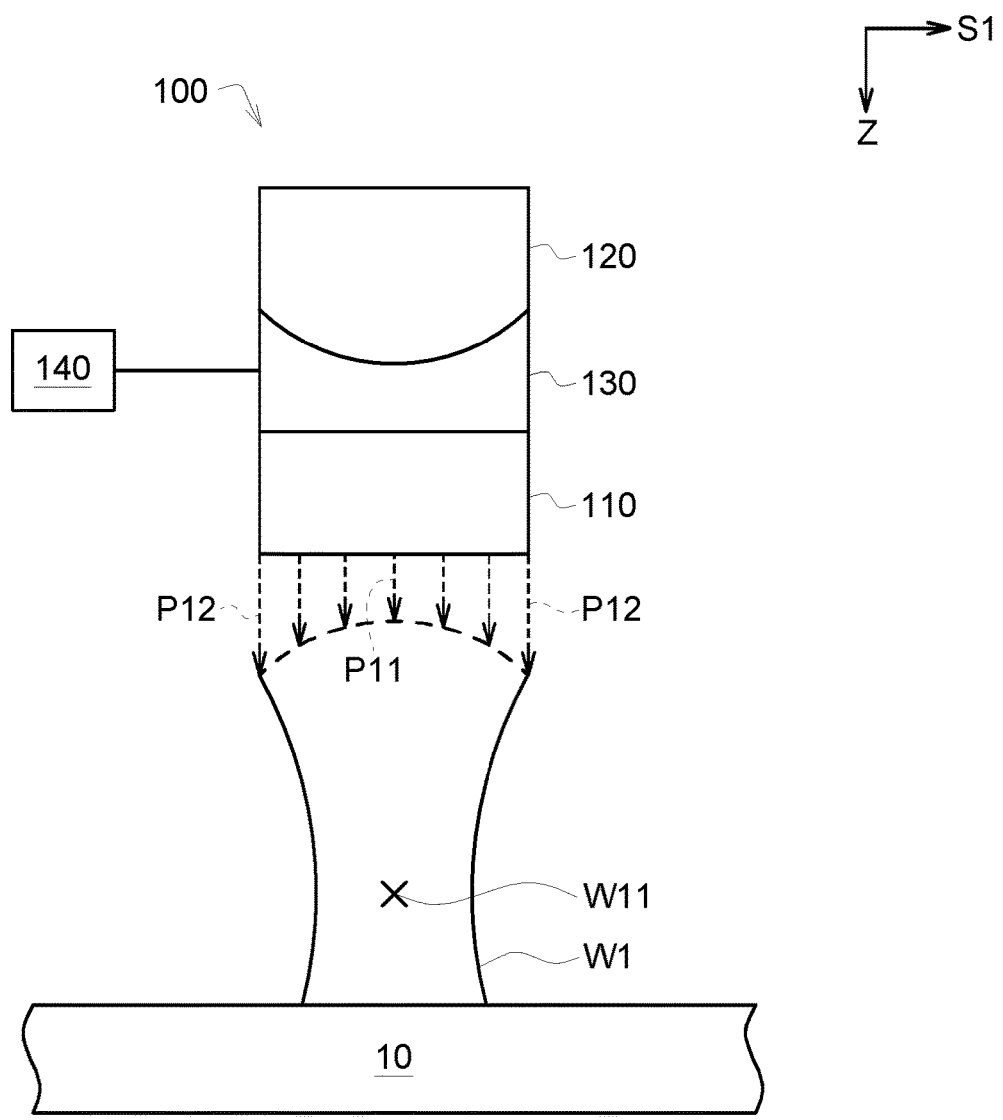
FIG. 2 is an assembly diagram of the ultrasound probe of FIG. 1.
Figure 3:
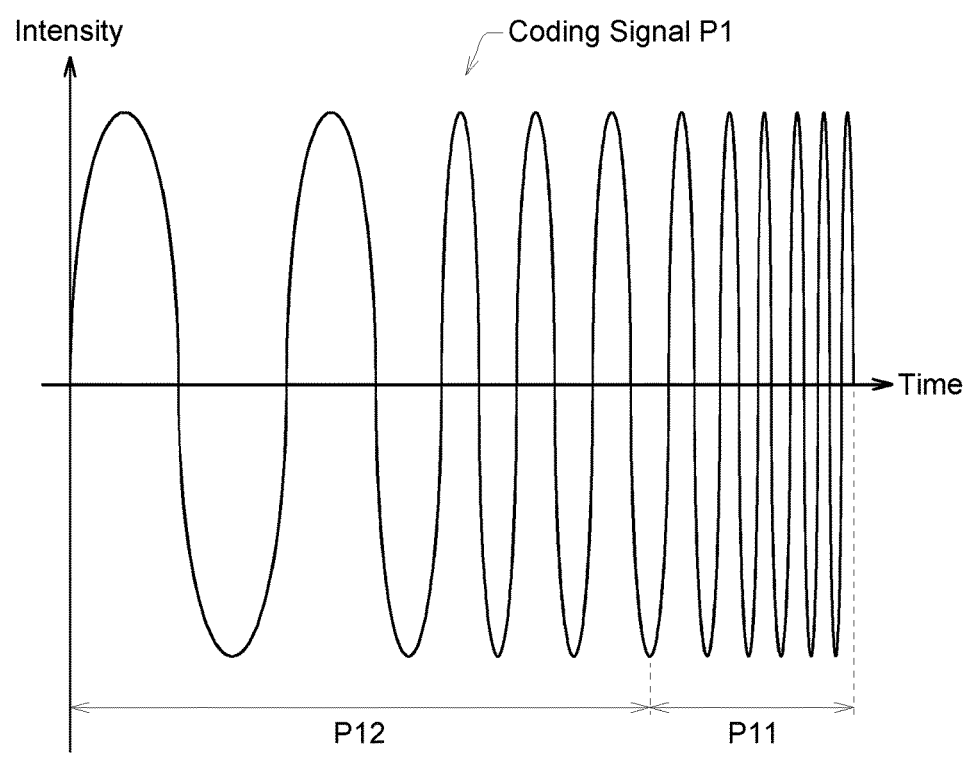
FIG. 3 is a waveform of a coding wave according to an embodiment of the invention.

Refer to FIGS. 1-3. FIG. 1 is a decomposition diagram of an ultrasound probe 100 according to an embodiment of the invention. FIG. 2 is an assembly diagram of the ultrasound probe 100 of FIG. 1. FIG. 3 is a waveform of a coding wave P1 according to an embodiment of the invention.

The ultrasound probe 100 includes a plurality of matching elements 110, a backing layer 120, a plurality of piezoelectric elements 130 and a driver 140.

The matching elements 110 may be made of material including epoxy mixing sliver powders, epoxy mixing aluminum oxide powders, etc. The matching elements 110 and ultrasound gel have an impedance in between that of the piezoelectric elements 130 and skin of a patient to reduce the amount of reflection at this interface and accordingly improve transmission into the patient.

The backing layer 120 may be made of material including polyurethane (PU), epoxy mixing tungsten powders, epoxy mixing carbon fibers, etc. The backing layer 120 can provide an effect on widening the bandwidth.

The piezoelectric element 130 has a concave surface $103s1$ and a plane $130s2$ disposed oppositely. The concave surface $103s1$ can be a curved surface, a plane or a combination thereof. The curved surface can be a circular curved surface, an elliptic curved surface or a curved surface with other geometric shape. The plane $130s2$ faces a detecting direction (exemplified by the +Z axis in the present embodiment), that is, the direction towards the analyte 10, and the concave surface $130s1$ backs to the detecting direction (the −Z axis). The backing layer 120 has a convex surface $120s1$ matching the concave surface $130s1$ of the piezoelectric element 130.

The piezoelectric element 130 is disposed between the matching element 110 and the backing layer 120. Each piezoelectric element 130 has an edge portion 131 and a middle portion 132.

The driver 140, such as a coding-wave driver, generates a coding wave P1 inputted to the piezoelectric element 130, such that the piezoelectric element 130 outputs a focusing sonic wave field W1 along a short axis S1 (as indicated in FIG. 2). The short axis S1 is a direction moving towards the middle portion 132 from the edge portion 131, and is substantially perpendicular to a long axis S2. The long axis S2 is the arrangement direction of a plurality of piezoelectric elements 130. The ultrasound probe 100 detects the properties of the analyte 10 through the focusing sonic wave field W1. The analyte 10 can be a living tissue (such as human or animal) or a non-living tissue.

In addition, the piezoelectric element 130 has a variable thickness t along a short axis S1 and correspondingly generates the focusing sonic wave field W1. That is, the field pattern of the focusing sonic wave field W1 varies with the thickness t of the piezoelectric element 130 along the short axis S1, such that different focusing sonic wave fields W1 can be used to detect different tissue portions or varieties. As indicated in FIG. 2, the focusing sonic wave field W1 has a focal spot W11 whose position varies with the thickness t of the piezoelectric element 130 along the short axis S1.

As indicated in FIG. 1, the thickness t2 of the middle portion 132 is smaller than the thickness t1 of the edge portion 131. For example, the thickness t of the piezoelectric element 130 diminishes in a direction towards the middle portion 132 from the edge portion 131. As indicated in FIG. 3, the coding wave P1 includes a high frequency wave-pattern P11 and a low frequency wave-pattern P12. The time sequence of the coding wave P1 is that the low frequency wave-pattern P12 comes before the high frequency wave-pattern P11. That is, the time sequence inputted to the piezoelectric element 130 is: low frequency wave-pattern P12 to high frequency wave-pattern P11, which means the low frequency signal enters the piezoelectric element 130 earlier than the high frequency signal. After entering the piezoelectric element 130, the low frequency signal resonates with the thicker portion and is transmitted outwards, and the high frequency signal resonates with the thinner portion and is transmitted outwards. Thus, the focusing sonic wave field W1 is generated.

Let FIG. 2 be taken for example. Since the time sequence of the coding wave P1 is that the low frequency wave-pattern P12 comes before the high frequency wave-pattern P11, the low frequency wave-pattern P12 enters the piezoelectric element 130 earlier than the high frequency wave-pattern P11. After entering the piezoelectric element 130, the low frequency wave-pattern P12 resonates with the thicker portion, that is, the edge portion 131, and then is transmitted towards the +Z axis; the high frequency wave-pattern P11 resonates with the thinner portion, that is, the middle portion 132, and then is transmitted towards the +Z axis. Regarding the time sequence by which the signal is transmitted outwards from the piezoelectric element 130, the low frequency wave-pattern P12 in the edge portion 131 with a larger thickness is transmitted outwards earlier than the high frequency wave-pattern P11 in the edge portion 131 with a larger thickness so as to generate the focusing sonic wave field W1. Here, the Z axis is basically perpendicular to the short axis S1 and the long axis S2, and the direction of the Z axis faces towards the analyte 10.

In addition, the coding wave P1 is adjustable, such that the piezoelectric element 130 can output a focusing sonic wave field W1 correspondingly modulated according to the adjustment of the coding wave P1. The field pattern of the focusing sonic wave field W1 and/or the position of the focusing sonic wave field W1 can be changed according to the adjustment. To put it in greater details, when the high frequency wave-pattern P11 and/or the frequency, amplitude and/or cycle of the low frequency wave-pattern P12 changes, the field pattern of the focusing sonic wave field W1 and/or the position of the focal spot W11 will change accordingly. For example, the focal spot W11 becomes farther away from or closer to the piezoelectric element 130 along the direction of the Z axis.

In an embodiment, the coding wave P1 can be a chirp coding wave, a barker coding wave, or a Golay coding wave. The coding wave P1 can be expressed in formula (1). In formula (1), $$g\left(t - \frac{T}{2}\right)$$

represents a Gauss function; $f_1$ represents a low frequency signal frequency; $f_2$ represents a high frequency signal frequency; T represents a signal cycle.

$$P1 = g\left(t - \frac{T}{2}\right)\cos\left(2\pi\left(f_1 t + \frac{f_2 - f_1}{2T} t^2\right)\right) \quad (1)$$

The piezoelectric element 130 can output a focusing sonic wave field W1 correspondingly modulated according to the design of the coding wave P1 and/or the thickness of the piezoelectric element 130 along the short axis S, such that the conventional acoustic lens can be dispensed with. That is, the matching element 110 does not need to have any acoustic lenses disposed thereon. In other words, the ultrasound probe 100 of the embodiment of the invention can be an ultrasound probe without having any acoustic lenses.

It can be understood from the above disclosure that the piezoelectric element 130 can output a focusing sonic wave field W1 correspondingly modulated according to the design of the coding wave P1 and/or the thickness of the piezoelectric element 130 to detect different varieties of tissues. Since the focusing sonic wave field W1 is outputted along the short axis S1, the ultrasound probe 100 of the embodiment of the invention can selectively dispense with the conventional acoustic lens.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An ultrasound probe, comprising:
   a matching element;
   a backing layer;
   a piezoelectric element disposed between the matching element and the backing layer and having a variable thickness along a short axis; and
   a driver;
   wherein the driver generates an adjustable coding wave inputted to the piezoelectric element, such that the piezoelectric element outputs a focusing sonic wave field correspondingly modulated according to the adjustment of the coding wave and the thickness of the piezoelectric element;
   wherein the piezoelectric element comprises an edge portion and a middle portion, the piezoelectric element has a thickness diminishing in a direction towards the middle portion from the edge portion, the coding wave comprises a high frequency wave-pattern and a low frequency wave-pattern, and the time sequence of the coding wave changes to the high frequency wave-pattern from the low frequency wave-pattern; and
   wherein the piezoelectric element has a concave surface and a plane opposite to the concave surface, the concave surface backs to a detecting direction, and the plane faces the detecting direction.

2. The ultrasound probe according to claim 1, wherein the high frequency wave-pattern are adjustable.

3. The ultrasound probe according to claim 1, comprising a plurality of piezoelectric elements arranged along a long axis, each piezoelectric element has a thickness changing along a short axis, and the focusing sonic wave field is emitted towards a detecting direction substantially perpendicular to the long axis and the short axis.

4. The ultrasound probe according to claim 1, wherein the piezoelectric element has a concave surface, the backing layer has a convex surface matching the concave surface.

5. An ultrasound probe, comprising:
   a matching element;
   a backing layer;

a piezoelectric element disposed between the matching
element and the backing layer; and a driver;

wherein the matching element does not have any acoustic lenses disposed thereon, and the driver generates a wave signal inputted to the piezoelectric element, such that the piezoelectric element outputs a focusing sonic wave field along a short axis;

wherein the piezoelectric element has a concave surface and a plane opposite to the concave surface, the concave surface backs to a detecting direction, and the plane faces the detecting direction.

6. The ultrasound probe according to claim 5, wherein the piezoelectric element comprises a middle portion and an edge portion, and the middle portion has a thickness smaller than that of the edge portion.

7. The ultrasound probe according to claim 5, wherein the coding wave comprises a high frequency wave-pattern and a low frequency wave-pattern, and the time sequence of the wave signal changes to the high frequency wave-pattern from the low frequency wave-pattern.

8. The ultrasound probe according to claim 5, wherein the driver is a coding-wave driver.

* * * * *